United States Patent [19]

Metz

[11] Patent Number: 4,715,995
[45] Date of Patent: Dec. 29, 1987

[54] PROCESS FOR THE PREPARATION OF ALKALI METAL AND ALKALINE EARTH SALTS OF BENZALDEHYDE-2,4-DISULFONIC ACID

[75] Inventor: Hans J. Metz, Heppenheim, Fed. Rep. of Germany

[73] Assignee: Hoechst Aktiengesellschaft, Frankfurt am Main, Fed. Rep. of Germany

[21] Appl. No.: 775,744

[22] Filed: Sep. 13, 1985

[30] Foreign Application Priority Data

Sep. 17, 1984 [DE] Fed. Rep. of Germany ....... 3434038

[51] Int. Cl.$^4$ .......................................... C07C 143/38
[52] U.S. Cl. .................................................... 260/511
[58] Field of Search ........................................ 260/511

[56] References Cited

U.S. PATENT DOCUMENTS 1,531,507  3/1925  Rosenbaum ........................ 260/511

FOREIGN PATENT DOCUMENTS

| 32238 | 3/1884 | Fed. Rep. of Germany . |
| 88952 | 2/1896 | Fed. Rep. of Germany . |
| 91818 | 2/1896 | Fed. Rep. of Germany . |
| 98321 | 1/1897 | Fed. Rep. of Germany . |
| 52-25732 | 2/1977 | Japan . |

OTHER PUBLICATIONS

Weygand/Hilgetag, "Preparative Organic Chemistry", John Wiley & Sons, New York, Gd. Hilgetag & Martini 1972, pp. 338-339.

Primary Examiner—Nicky Chan

[57] ABSTRACT

The invention consists in a single-pot process for the preparation of benzaldehyde-2,4-disulfonic acid salts from 2,4-dichlorobenzal chloride, 2,4-dichlorobenzal chloride being reacted with an aqueous solution of an alkali metal or alkaline earth sulfite and/or hydrogensulfite in the presence of acid-bonding substances at 140°-180° C. Benzaldehyde-2,4-disulfonic acid and its salts are used in the electroplating industry and in the preparation of triphenylmethane dyestuffs.

15 Claims, No Drawings

PROCESS FOR THE PREPARATION OF ALKALI METAL AND ALKALINE EARTH SALTS OF BENZALDEHYDE-2,4-DISULFONIC ACID

The invention relates to a process for the preparation of alkali metal and alkaline earth salts of benzaldehyde-2,4-disulfonic acid from 2,4-dichlorobenzal chloride.

Benzaldehyde-2,4-disulfonic acid and its salts constitute valuable technical products and, for example, find application in the electroplating industry and in the production of triphenylmethane dyestuffs.

Until now only a two-stage process method has been known for the preparation of the disodium salt of benzaldehyde-2,4-disulfonic acid from 2,4-dichlorobenzal chloride.

1. Preparation of 2,4-dichlorobenzaldehyde from 2,4-dichlorobenzal chloride.
2. Reaction of the 2,4-dichlorobenzaldehyde obtained with sodium sulfite and/or hydrogensulfite.

According to the state of the art several methods are available for carrying out the first stage. For example, 2,4-dichlorobenzal chloride is converted to the bisulfite compound of the aldehyde using a mixture of concentrated sulfuric acid and oleum at 40°-50° C., the aldehyde is liberated by means of soda solution and extracted by steam distillation (see German Reich Patent No. 32,238 and Liebigs Ann. 260, 68).

The direct hydrolysis of 2,4-dichlorobenzal chloride using zinc oxide as a catalyst at 110°-140° C. may also be mentioned in addition (see Japanese Offenlegungsschrift No. 77/25733).

The state of the art of the second stage is given by the German Reich Patent Nos. 88,952, 91,818 and 98,321.

Thus, German Reich Patent No. 88,952 describes the reaction of 2-chlorobenzaldehyde with an aqueous sodium hydrogensulfite solution at reaction temperatures of 190°-200° C. and with reaction times of 8 h to form the sodium salt of benzaldehyde-2-sulfonic acid. According to the German Reich Patent No. 91,818, the sodium salt of 5-chlorobenzaldehyde-2-sulfonic acid is obtained in an analogous manner from 2,5-dichlorobenzaldehyde. Finally, in German Reich Patent No. 98,321 an analogous method is described for the preparation of an aqueous solution of the disodium salt of benzaldehyde-2,4-disulfonic acid from 2,4-dichlorobenzaldehyde at reaction temperatures of 190°-200° C. and with reaction times of 9-10 h. The substance is, however, not isolated in this process, and there are no data on yield. In carrying out the reaction under the conditions specified in the example in the German Reich Patent No. 98,321 a large proportion of by-products is produced. Dark colored heterogeneous reaction mixtures are obtained, from which strongly contaminated product can be isolated only with considerable effort with a yield of 30-60% of theory.

The overall process involving two stages suffers from the disadvantages of the low yield, poor reproducibility and, in spite of intermediate isolation, of a low degree of purity of the desired product.

The objective therefore was to develop a suitable method which yields in a reproducible manner the desired product with economic yields.

A process has now been found for the preparation of an alkali metal or an alkaline earth salt of benzaldehyde-2,4-disulfonic acid from 2,4-dichlorobenzal chloride, wherein 2,4-dichlorobenzal chloride is reacted with an alkali metal or alkaline earth sulfite and/or hydrogensulfite in the presence of water and acid-bonding substances, preferably at pH of 7-12 and at a temperature of 140°-180° C., preferably 160°-170° C.

Substituted benzal chlorides and benzaldehydes are reactive compounds which, particularly in an alkaline environment, are subject to a very wide variety of reactions, e.g. condensation reactions or the Cannizzaro reaction. It is therefore extremely surprising that, in spite of the diverse reaction possibilities in the system 2,4-dichlorobenzal chloride/2,4-dichlorobenzaldehyde/sulfite (or hydrogensulfite)/water/acid-bonding substance, the desired product is formed with absolute predominance. It was further found that, contrary to the teaching of the patents cited above on the reaction with sulfite, the optimum reaction temperature is below 180° C., preferably at 160°-170° C., and that, in spite of the lower temperature, a reaction time of less than 7 h, preferably of only 2-4 h, is adequate.

Under the reaction conditions according to the invention the aldehyde group is formed and the sulfonic acid radicals are introduced by means of the sulfite. The hydrochloric acid liberated in the formation of the aldehyde group is neutralized by the buffer substance present in the reaction mixture. For this purpose the sodium or potassium carbonate, sodium or potassium hydrogencarbonate, magnesium or calcium carbonate, magnesium or calcium hydrogencarbonate, calcium hydroxide or lime water, sodium or potassium phosphate or excess sulfite are, for example, suitable.

It is expedient to proceed in a manner such that 2,4-dichlorobenzal chloride is heated together with the buffer substance and an aqueous solution of the sulfite and/or hydrogensulfite in a closed vessel while being stirred. As sulfites and hydrogensulfites those of sodium and potassium come up in particular for consideration.

The cation of the sulfite should be the same as that of the hydrogensulfite and that of the salt used as buffer substance in order to obtain a uniform product.

The sulfite and/or hydrogensulfite is used with advantage in a quantity of 2-2.5 moles, preferably 2.05-2.15 moles, per mole of 2,4-dichlorobenzal chloride.

The suitable mass ratio of sulfite and/or hydrogensulfite to water depends partly on its solubility. In the case of sodium sulfite the mass ratio is preferably 0.11-0.33, in particular 0.22-0.25.

The pH of the reaction mixture should preferably be between 7 and 12.

Expediently, to isolate the reaction product a part of the water is distilled off and the product is allowed to crystallize out during cooling.

Excess sulfite and/or hydrogensulfite can be removed by conventional methods. Oxidation with aqueous sodium hypochlorite solution after the crystallization of the product may be mentioned as preferred. The reaction product can be separated from the mother liquor in a simple manner by centrifuging.

The advantages of the new procedure compared with the state of the art lie in the lower cost of the single-stage process, in the reproducibility, high yield, saving of energy as a result of a considerably shortened reaction time and substantially increased space-time yield.

EXAMPLE 1

230 g (1 mole) of 2,4-dichlorobenzal chloride are heated in a closed vessel together with a solution of 260 g (2.06 moles) of sodium sulfite and 85 g (0.8 mole) of sodium carbonate in 1,040 g of water for 3.5 h at 170° C.

After concentration to 70% by weight of the initial weight an oxidation with 140 g of sodium hypochlorite solution (13% by weight of NaOCl) 307 g of product is obtained by centrifuging, with a content of 74.4% by weight of disodium benzaldehyde-2,4-disulfonate (=73.5% of theory).

EXAMPLE 2

230 g (1 mole) of 2,4-dichlorobenzal chloride are heated in a closed vessel together with a solution of 260 g (2.06 moles) of sodium sulfite and 180 g (2.14 moles) of sodium hydrogencarbonate in 1,045 g of water for 3.5 h at 170° C. After concentration to 70% of the initial weight and oxidation with 140 g of sodium hypochlorite solution (13% by weight of NaOCl), 313 g of product is obtained by centrifuging, with a content of 74.9% of disodium benzaldehyde-2,4-disulfonate ( 75.6% of theory).

I claim:

1. A process for the preparation of an alkali metal or alkaline earth metal salt of benzaldehyde-2,4-disulfonic acid from 2,4-dichlorobenzal chloride, which comprises reacting 2,4-dichlorobenzal chloride with an alkali metal or alkaline earth metal sulfite or an alkali metal or alkaline earth metal hydrogensulfite, or a mixture of any of these salts, in the presence of water and an acid-bonding substance at a temperature of 140° C. to below 180° C.

2. A process according to claim 1, wherein the reaction is carried out at 160°-170° C.

3. A process according to claim 1, wherein the reaction is carried out at a pH of 7-12.

4. A process according to claim 2, wherein the reaction is carried out at a pH of 7-12.

5. A process according to claim 1, wherein 2-2.5 moles of the sulfite and/or hydrogensulfite, in the form of an aqueous solution, are used per mole of starting compound.

6. A process according to claim 2, wherein 2-2.5 moles of the sulfite and/or hydrogensulfite, in the form of an aqueous solution, are used per mole of starting compound.

7. A process according to claim 3, wherein 2-2.5 moles of the sulfite and/or hydrogensulfite, in the form of an aqueous solution, are used per mole of starting compound.

8. A process according to claim 4, wherein 2-2.5 moles of the sulfite and/or hydrogensulfite, in the form of an aqueous solution, are used per mole of starting compound.

9. A process according to claim 1, wherein sodium carbonate and/or sodium hydrogencarbonate is used as the acid-bonding substance.

10. A process according to claim 1, wherein an aqueous sodium sulfite solution is used with a mass ratio of sodium sulfite to water of 0.11 to 0.33.

11. A process according to claim 2, wherein an aqueous sodium sulfite solution is used with a mass ratio of sodium sulfite to water of 0.11 to 0.33.

12. A process according to claim 3, wherein an aqueous sodium sulfite solution is used with a mass ratio of sodium sulfite to water of 0.11 to 0.33.

13. A process according to claim 5, wherein an aqueous sodium sulfite solution is used with a mass ratio of sodium sulfite to water of 0.11 to 0.33.

14. A process according to claim 8, wherein an aqueous sodium sulfite solution is used with a mass ratio of sodium sulfite to water of 0.11 to 0.33.

15. A process according to claim 9, wherein an aqueous sodium sulfite solution is used with a mass ratio of sodium sulfite to water of 0.11 to 0.33.

* * * * *